US012569130B2

(12) United States Patent
Abdal et al.

(10) Patent No.: US 12,569,130 B2
(45) Date of Patent: Mar. 10, 2026

(54) SYSTEM AND METHOD FOR MANAGING AMBLYOPIA AND SUPPRESSION

(71) Applicant: Kanohi Eye Private Limited, Maharashtra (IN)

(72) Inventors: Md Oliullah Abdal, West Bengal (IN); Rajesh Prakash Kotwani, Maharashtra (IN); Gul Jagdish Nankani, Maharashtra (IN); Sonia Gul Nankani, Maharashtra (IN); Vijay Srichand Talreja, Maharashtra (IN)

(73) Assignee: Kanohi Eye Private Limited, Maharashtra (IN)

( * ) Notice: Subject to any disclaimer, the term of this patent is extended or adjusted under 35 U.S.C. 154(b) by 238 days.

(21) Appl. No.: 16/998,936

(22) Filed: Aug. 20, 2020

(65) Prior Publication Data

US 2021/0275011 A1 Sep. 9, 2021

(30) Foreign Application Priority Data

Mar. 7, 2020 (IN) .............................. 202021009871

(51) Int. Cl.
 *A61B 3/024* (2006.01)
 *A61B 3/00* (2006.01)
 *A61B 3/02* (2006.01)
 *A61B 3/032* (2006.01)
 (Continued)

(52) U.S. Cl.
 CPC ............. *A61B 3/032* (2013.01); *A61B 3/0041* (2013.01)

(58) Field of Classification Search
 CPC ......... A61B 3/02; A61B 3/102; A61B 3/1025; A61B 3/113; A61B 3/1015; A61B 3/024; A61B 3/032; A61B 3/022; G09B 23/30

USPC ............... 351/237, 200, 205, 206, 209, 210, 351/221–223, 239, 240, 243, 246, 201; 434/271; 600/558
See application file for complete search history.

(56) References Cited

U.S. PATENT DOCUMENTS 8,913,905 B2 * 12/2014 Shiomichi .......... G03G 15/5062
                                                   399/15
11,730,357 B2 8/2023 Ooi et al.
 (Continued)

FOREIGN PATENT DOCUMENTS

WO 2008/070683 A1 6/2008
WO 2019/100165 A1 5/2019

*Primary Examiner* — Dawayne Pinkney
(74) *Attorney, Agent, or Firm* — Workman Nydegger

(57) ABSTRACT

Approaches for implementing therapeutic activities comprising visual challenges and tasks for improving visual acuity and stereoscopic acuity for management of binocular vision disorders are described. In an example, the computing device may generate two sets of visual elements with different visual characteristics, with each set corresponding to each eye of the user. The visual elements may be displayed based on values of element attributes such as contrast, size, spatial frequency and speed. The user may then be prompted to provide a response. Based on received user's response, the element attributes may be modified, and new sets of visual elements may be displayed. In another example, visual elements with two images separated by a certain offset may be displayed. The user may be prompted to provide a response. Based on user's response, the offset value of one of the visual elements may be modified and modified visual elements may be displayed.

9 Claims, 6 Drawing Sheets

(51) Int. Cl.
    *A61B 3/10*           (2006.01)
    *A61B 3/12*           (2006.01)

(56)                References Cited

U.S. PATENT DOCUMENTS

| | | | |
|---|---|---|---|
| 2008/0212032 A1* | 9/2008 | Seiller | G09B 19/0038 |
| | | | 351/222 |
| 2008/0309879 A1* | 12/2008 | Hirji | A61B 3/032 |
| | | | 351/239 |
| 2010/0073469 A1 | 3/2010 | Fateh | |
| 2010/0201942 A1* | 8/2010 | Hess | H04N 13/327 |
| | | | 351/203 |
| 2010/0283969 A1* | 11/2010 | Cooperstock | A61B 3/022 |
| | | | 351/201 |
| 2011/0027766 A1* | 2/2011 | Yoo | A61B 3/032 |
| | | | 434/262 |
| 2011/0149238 A1* | 6/2011 | Zhang | A61B 3/14 |
| | | | 351/203 |
| 2016/0270656 A1* | 9/2016 | Samec | G02B 27/0179 |
| 2016/0302991 A1 | 10/2016 | Vadai et al. | |
| 2017/0164822 A1* | 6/2017 | Kalder | A61B 3/0041 |
| 2017/0340200 A1* | 11/2017 | Blaha | A61B 3/113 |
| 2017/0351326 A1* | 12/2017 | Aarts | G02B 27/017 |
| 2019/0125180 A1* | 5/2019 | Arnold | A61B 3/113 |
| 2019/0159956 A1 | 5/2019 | Koziak | |
| 2020/0054205 A1* | 2/2020 | Gaier | A61B 3/0058 |

* cited by examiner (B)

(A)

SYSTEM AND METHOD FOR MANAGING AMBLYOPIA AND SUPPRESSION

CROSS-REFERENCE TO RELATED APPLICATIONS

This application claims the benefit of and priority to India application No. 202021009871, filed on Mar. 7, 2020 entitled "SYSTEM AND METHOD FOR MANAGING AMBLYOPIA AND SUPPRESSION," the content of which is incorporated herein by reference in its entirety.

BACKGROUND

Owing to the necessity and complexity involved with the functions performed by human eyes, it may be crucial to treat visual disorders accurately and properly. A variety of visual disorders may affect the eye, examples of which include amblyopia and a condition referred to as suppression. A patient with amblyopia and suppression suffers from neuro-visual developmental disorder of the eye. Amblyopia and suppression can be treated conventionally using occlusion therapy by patching the non-amblyopic eye, while a set of visual challenges and inputs may be provided to the patient to train the amblyopic eye. The training of the afflicted eye, over a period of time, may result in neuro-vision development.

BRIEF DESCRIPTION OF THE DRAWINGS

The following detailed description references the drawings, wherein.

Figure 1:
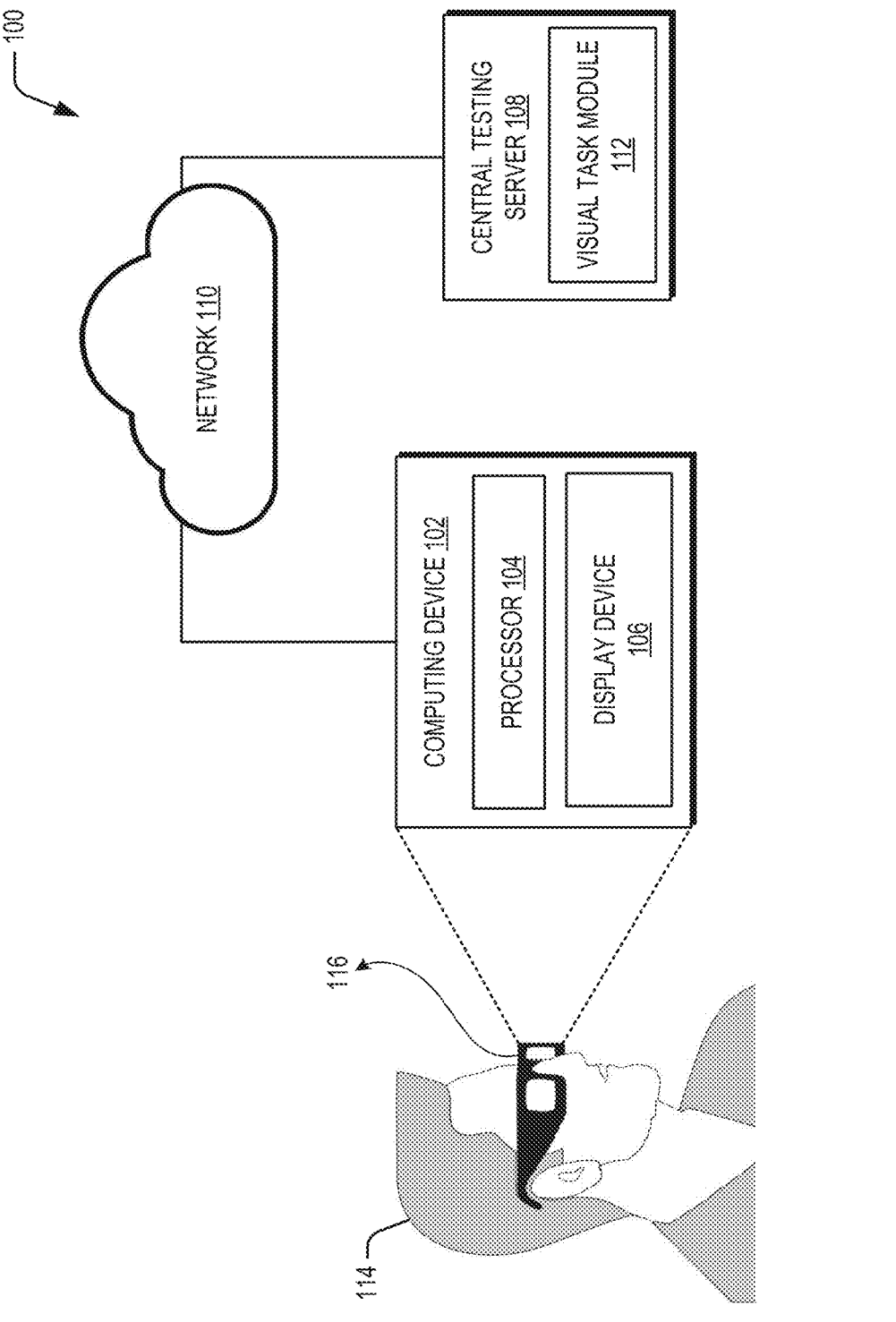
FIG. 1 illustrates an exemplary computing environment implementing therapeutic activities for management of binocular vision disorders, as per an example of the present subject matter.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION

Eyes are one of the most essential part of a human body. The eyes detect the incoming light from the surroundings.

Thereafter, various nerve endings present in the anatomy of the eyes may convert the detected light into electrical signals. Such signals may be processed by the human brain to create visual perception of surrounding objects.

An individual may, in certain instances, suffer from vision disorders. Examples of vision disorders may include, but are not limited to, disorders pertaining to refractive errors, cataract, strabismus, and misalignment of eyes. One such vision disorder is amblyopia. In amblyopia, the patient may suffer from vision development disorder in at least one of the two eyes. Amblyopia may be caused in the patient due to improper neural development of the optic nerve of one of the eyes.

Owing to the improper neural development of one of the eyes, referred to as amblyopic or weak eye, the patient's brain may favour and process neurological input from only one eye, referred to as non-amblyopic or dominant eye and may tend to discard the visual input from the other eye, referred to as amblyopic or weak eye. As a result, the patient's brain may then subconsciously tend to adapt to avoid such vision disorders and may tend to further suppress the neurological input from the amblyopic eye. Such a condition is referred to as suppression.

As a result, the patient may suffer from blur vision from the amblyopic eye and thereby, the patient's brain may have difficulty combining the visual inputs from both the eyes. Although, both the eyes of patient may detect incoming light from the surroundings, the brain may still not be able to properly perceive the surroundings. As a result, the patient may experience difficulty in development of binocular vision, and the patient may not be able to perceive depth properly.

Various conventional approaches provide a variety of treatments to treat amblyopia and suppression. One such conventional approach involves occlusion therapy. Occlusion therapy includes covering the non-amblyopic eye, i.e., the normal eye with a patch. The patient may then be required to perform certain visual exercises with the amblyopic eye, or the amblyopic eye may be subjected to visual challenges. Examples of such exercises may include, but are not limited to, requiring the patient to focus on an object with the amblyopic eye for a certain amount of time and requiring the patient to align a series of objects along a straight line, such as aligning beads on a thread. On the other hand, examples of conventional visual challenges may include, but are not limited to, focusing on a moving object with the weak eye.

Such exercises and treatments, over a period of time improves the cognitive capability of the brain for processing the visual inputs from the weak eye. Since the weak eye is subjected to the visual challenges, the patient's brain is conditioned to receive visual inputs from the amblyopic eye and process them, thereby improving the neural and visual development of the patient's amblyopic eye.

The above approaches have been found to be useful, but as such, subjecting the patient to wear the patch for prolonged interval is not possible for cases where the patient is suffering from severe amblyopia. Further, it may not be convenient for a child to wear a patch owing to the psychological and social difficulty.

Owing to the conventional approaches involved in treatment of amblyopia and suppression using occlusion therapy, the treatment results may sometimes vary and may not correlate with the clinical conditions of the patient. As a result, patching one of the eyes and treating amblyopia in the patient using occlusion therapy may show slow improvements, and sometimes may not show any improvement in older children and adults. Further, occlusion therapy may not show complete improvements and may result in residual amblyopia. The patient's vision may not improve despite subjecting the patient repeatedly to occlusion therapy.

Moreover, patching one of the eyes and then subjecting it to the visual inputs, may only tend to improve the vision of the weak eye, i.e., the visual acuity but may not improve the depth perception ability, i.e., the stereoscopic acuity of the patient's eyes. Furthermore, it may also be the case that patients may again develop binocular vision disorders, i.e., amblyopia and suppression after a certain time has elapsed post completing the occlusion therapy.

Example systems for performing therapeutic activities for management of binocular vision disorders are described. In one example, different set of therapeutic activities for improving the visual acuity, fusional capability and stereoscopic acuity of the user may be implemented using a computing device. To this end, for improving visual acuity, the computing device may generate two sets of visual elements, with one set corresponding to one eye of the user and the other set corresponding to the other eye. The visual elements in turn may possess different visual characteristics. Examples of visual characteristics include chromaticity and polarity. In a same manner, for improving fusional capability and stereoscopic acuity, the computing device may generate a plurality of visual elements, wherein such visual elements comprise two images that are separated by a certain offset with respect to each other.

For improving visual acuity, the computing device may display the two sets of the visual elements on a display device. The visual elements may further be defined using a set of element attributes. The element attributes of the visual elements may include their size, contrast, spatial frequency and speed. The different visual elements may be rendered on the display device as part of a visual challenge (e.g., a game). Thereafter, a user may provide a response to the visual challenge. Based on the user's responses to the visual challenge, the values of element attributes of the visual elements may be modified and accordingly displayed. For example, with progressive series of responses, the visual elements may be displayed more frequently, or with a different size and different contrast.

For improving fusional capability and stereoscopic acuity, visual elements with two images separated by an offset may be provided. The two images may be defined based on a certain attribute. The user is provided with dissociative glasses to interact and engage with the visual elements being displayed on the screen. Based on the response of the user, the offset distance between the two images of the visual elements may be changed.

The present subject matter is further described with reference to the accompanying figures. Wherever possible, the same reference numerals are used in the figures and the following description to refer to the same or similar parts. It should be noted that the description and figures merely illustrate principles of the present subject matter. It is thus understood that various arrangements may be devised that, although not explicitly described or shown herein, encompass the principles of the present subject matter. Moreover, all statements herein reciting principles, aspects, and examples of the present subject matter, as well as specific examples thereof, are intended to encompass equivalents thereof.

The words during, while, and when as used herein are not exact terms that mean an action takes place instantly upon an initiating action but that there may be some small but reasonable delay, such as propagation delay, between the initial action and the reaction that is initiated by the initial action. Additionally, the words "connected" and "coupled" are used throughout for clarity of the description and can include either a direct connection or an indirect connection. Various examples of the present subject matter have been described below by referring to several examples.

The manner in which the example therapeutic activities are implemented on a computing device are explained in detail with respect to FIGS. 1-6. It is to be noted that drawings of the present subject matter shown here are for illustrative purposes and are not to be construed as limiting the scope of the subject matter claimed.

FIG. 1 illustrates an exemplary computing environment 100, comprising a computing device 102. The computing device 102 implements therapeutic activities for management of binocular vision disorders, as per an example of the present subject matter. The computing device 102, in an example, may be any computing device capable of receiving user's inputs, processing it, and displaying output information based on the received user's inputs. Examples of such computing devices may include, but are not limited to, a personal computer, a handheld computer, a mobile device, and a portable computer.

The computing device 102 further includes a processor 104, and display device 106. The display device 106 may be coupled to the computing device 102 (as a standalone display) or may be integrated within the computing device 102 (as a display panel of a laptop or a tablet computer). The computing device 102 may be further connected to a central testing server 108 over a network 110. The central testing server 108 may include a visual task module 112. In one example, the visual task module 112 may be implemented within the computing device 102, without deviating from the scope of the present subject matter.

Amongst other things, the central testing server 108 may further include programmable instructions which when executed, may cause generation of one or more visual elements to be displayed on the display device 106. It may be noted that such programmable instructions correspond to therapeutic activities for improving the visual and stereoscopic acuity for managing binocular vision disorders, such as amblyopia and suppression. The visual elements thus generated on the display device 106 may be in the form of visual challenges (e.g., a game) requiring interaction and inputs from a user, e.g., the user 114, during a session. Initially, the visual elements may be generated based on certain pre-defined criteria, which may be changed in-session depending on the inputs received from the user 114. The user 114 may be required to perform the activity with a pair of dissociative glasses 116. Such dissociative glasses 116 aid in filtering a set of visual elements for one eye, such that both eyes receive different visual inputs.

In operation, the user 114 or any other authorized individual may initiate the activity. In response to the initiation, the visual task module 112 may generate display signals corresponding to the visual challenges pertaining to the activity which is to be performed. The corresponding display signals may be transmitted to the computing device 102, wherein on the display device 106, visual elements conforming to the display signals may be generated. The visual elements may be a part of a series of dynamically changing visual challenges and tasks intended for the user 114.

In an example, for improving the visual acuity of the user, the computing device 102 may generate two sets of visual elements, corresponding to each eye of the user. The two sets of visual elements may comprise different visual characteristics. Examples of such visual characteristics include chromaticity and polarity. The two sets of visual elements may be displayed on the display device 106 based on a set of values of element attributes. The element attributes of the visual elements may control and determine the way in which the visual elements may be displayed on the display device 106. The element attributes may include size, contrast, spatial frequency and speed of the two sets of visual elements. The initial values may correspond to the clinical parameters of the user.

In another example, for improving the fusional capability and stereoscopic acuity of the user, the computing device 102 may generate a set of visual elements with two images separated by an offset value. The two images may comprise different visual characteristics. Examples of such visual characteristics include chromaticity and polarity. The two images may be displayed on the display device 106 based on a certain pre-defined offset. The offset is such that it, along with a notional line passing through the two eyes of the user, lies in the same horizontal plane. The offset value of the two images of a certain visual element may control the depth at which the corresponding visual element may be displayed on the display device 106. The user may be provided with dissociative glasses to interact and engage with the visual elements being displayed on the screen. It may be noted that, the user may be required to view the visual elements at a viewing direction perpendicular to that of the display device 106.

Returning to the present example, the computing device 102 may then prompt the user 114 to provide a response. The user may provide the response through a peripheral device (not shown in FIG. 1). As would be understood, the visual elements displayed on the display device 106 comprising the visual challenges and tasks in the activity may prompt the user to provide a response at every stage of the activity. The computing device 102, on receiving the user's responses may transmit them to the visual task module 112 over the network 110.

The visual task module 112, on receiving the user's response, may compare the response using a pre-defined assessment criteria to ascertain whether the user's response is correct or not, and also determine how quickly the response was provided by the user 114. The visual task module 112 may also determine to ascertain the accuracy of user's responses for a pre-defined number of times.

In one example, for improving the visual acuity, when the user 114 provides a series of correct responses, the visual task module 112 modifies the element attributes, i.e., size, spatial frequency, contrast and speed of the two sets of visual elements in such a manner, so as to increase the difficulty of the visual challenges of the therapeutic activity. Thereafter, the visual task module 112 may generate display signals corresponding to the modified values of element attributes and transmit them to the computing device 102. The display signals may then cause the display device 106 to generate two sets of modified visual elements.

In another example for improving the fusional capability and stereoscopic acuity, when the user 114 provides a correct response, the visual task module 112 may modify the offset distance between the two images of at least one of the sets of displayed visual elements. The offset value may be modified in such a manner, so as to modify the depth at which one of the visual elements may be displayed. Thereafter, the visual task module 112 may generate display signals corresponding to the modified offset value and transmit them to the computing device 102. The display signals may then cause the display device 106 to generate modified visual elements.

In this manner, as the series of visual challenges progresses, the user on providing a series of correct responses may continuously cause the visual task module 112 to modify the element attributes, generate display signals and display the modified set of visual elements on the display device 106. The successive sets of modifying visual elements cause the amblyopic eye, i.e., the weak eye to focus on the visual elements, thereby improving the visual acuity, fusional capability, and stereoscopic acuity of the user. Further, since both the eyes of the user are subjected to the sets of visual elements, the approaches described in the present subject matter improves both the eyes of the user simultaneously. These and other aspects are described in further details below, in conjunction with FIG. 2.

Figure 2:
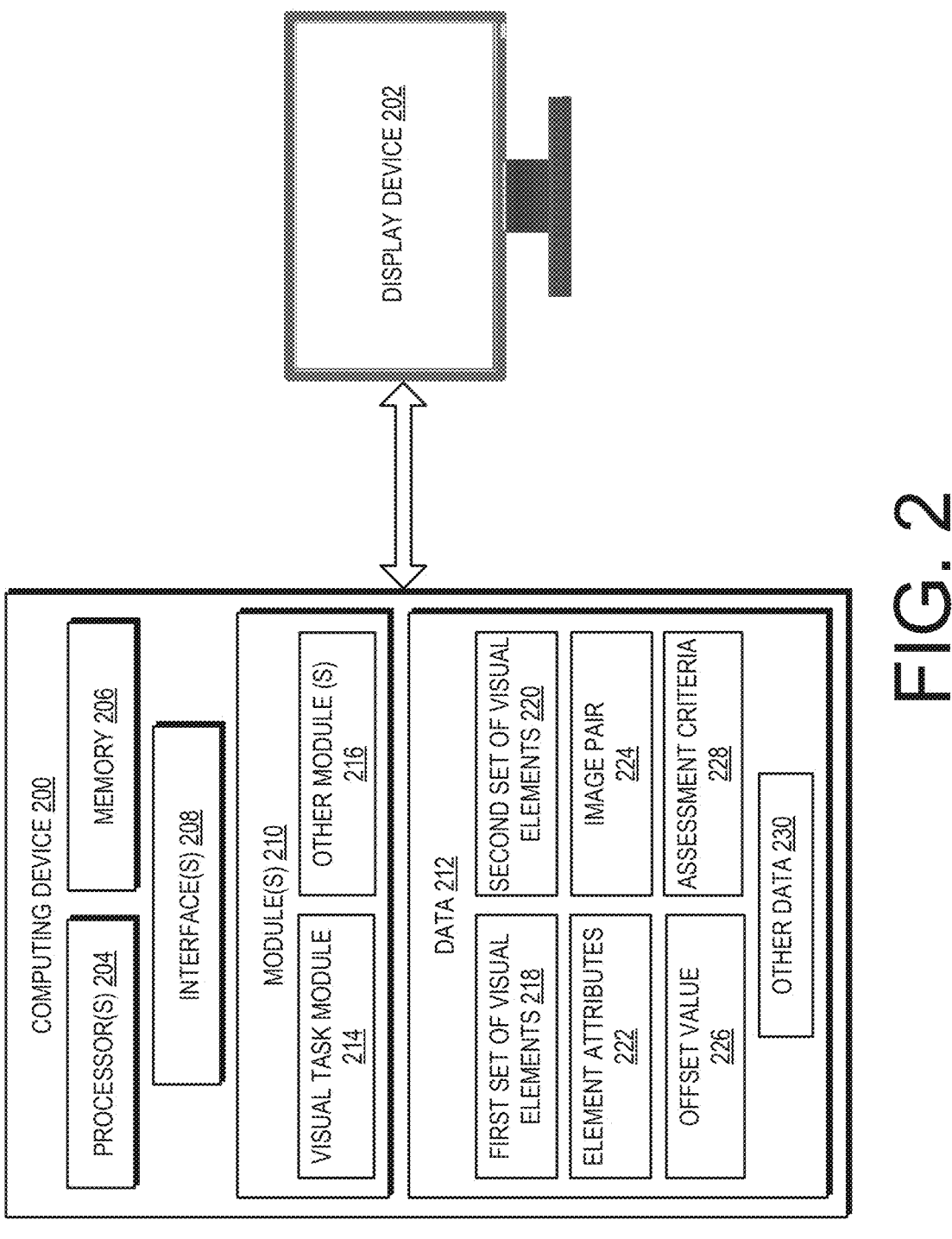
FIG. 2 is a block diagram of an example computing device for implementing therapeutic activities for management of binocular vision disorders, as per an example of the present subject matter.

FIG. 2 illustrates a block diagram of an example computing device for implementing therapeutic activities for management of binocular vision disorders, as per an example of the present subject matter. The computing device 200 may be coupled to a display device 202. Further, a peripheral input device (not shown in FIG. 2) may also be coupled to the computing device 200 for capturing user's inputs.

The computing device 200 may be implemented as any computing device with an input device for capturing user's inputs and with a display, capable of rendering the therapeutic activities for management of binocular vision disorder. In one example, the computing device may include a personal computer, coupled to a display device. Examples of such display devices may include, but are not limited to, LED display, projector, and/or any other display device capable of rendering objects based on some signals. In another example, the computing device 200 may be implemented as a portable computer, notebook PC, mobile phone, handheld device, etc.

The computing device 200 may include processor(s) 204, a memory 206, and an interface(s) 208. The processor(s) 204 may be implemented as signal processor(s), state machine(s), logic circuitries, and/or any other device or component that manipulate signals based on operational instructions.

The memory 206 may store one or more computer-readable instructions. The memory 206 may include any non-transitory computer-readable medium including, for example, volatile memory such as RAM, or non-volatile memory such as EPROM, flash memory, and the like. The interface(s) 208 may include a variety of interfaces, for example, interface for data input and output devices, referred to as I/O devices, storage devices, network devices, and the like, for communicatively associating the computing device 200 with interface of any other computing device.

The computing device 200 may further include module(s) 210 and data 212. The module(s) 210 may be implemented as a combination of hardware and programming logic (e.g., programmable instructions) to implement one or more functionalities of the module(s) 210. In one example, the module(s) 210 may include a visual task module 214 for generating and performing therapeutic activities. The module(s) 210 may further include other module(s) 216. The data 212 on the other hand includes first set of visual elements 218, second set of visual elements 220, element attributes 222, image pair 224, offset value 226, assessment criteria 228 and other data 230. Further, the other data 230, amongst other things, may serve as a repository for storing data that is processed, or received, or generated as a result of the execution of one or more modules in the module(s).

In examples described herein, such combinations of hardware and programming may be implemented in a number of different ways. For example, the programming for the module(s) 210 may be processor executable instructions stored on a non-transitory machine-readable storage medium and the hardware for the module(s) 210 may include a processing resource (e.g., one or more processors), to execute such instructions. In the present examples, the machine-readable storage medium may store instructions that, when executed by the processing resource, implement module(s) 210 or their associated functionalities.

In operation, the user or any other authorized individual (not shown in FIG. 2) may initiate one of the plurality of therapeutic activities for management of binocular vision disorder. In response to the initiation, the visual task module 214 may generate display signals corresponding to the visual challenges pertaining to the activity which is to be performed. The visual elements may then be displayed on the display device 202. The therapeutic activity may include a series of dynamically changing visual challenges and tasks (e.g., a game) requiring interactions and inputs from the user for improving the visual acuity, fusional capability, and stereoscopic acuity.

In one example, for improving the visual acuity of the user, the visual task module 214, in response to the initiation, may generate a first set of elements 218 and a second set of elements 220, configured for each eye of the user. The two set of visual elements may be a part of series of dynamically changing visual challenges and tasks intended for the user and may comprise different visual characteristics and element attributes 222. The element attributes 222 may include size, contrast, spatial frequency and speed of the two sets of visual elements 218 and 220 and may control the manner in which the two sets of visual elements may be displayed on the display device 202.

The user may be required to perform the activities with a pair of dissociative glasses. Examples of such dissociative glasses may include, but are not limited to, a pair of anaglyph glasses and polaroid glasses. The dissociative glasses aid in filtering a set of visual elements for one eye, such that both eyes receive different visual inputs.

In one example, the user may perform the activity with a pair of chromatically different coloured anaglyph glasses. In such cases, the different visual characteristic of the two sets of visual elements may correspond to the different colours of the anaglyph glasses. Examples of anaglyph glasses may include, but are not limited to, a pair of red and blue coloured glasses, red and cyan coloured glasses, and green and red coloured glasses.

Furthermore, the user may be required to calibrate the anaglyph glasses before proceeding with the therapeutic activity. In one example, the user may have to locate a pair of differently coloured objects, corresponding to the colour filters of anaglyph glasses. In another example, the user may require matching the contrast of the colours used in anaglyph glasses to the contrast of the image displayed on the display device 202.

It may be noted that, the anaglyph glasses may be calibrated so as to enable the user to perform the therapeutic activities efficiently, and thereby allowing the eye care practitioner to assess the results in an efficient manner. The visual characteristics of the two sets of visual elements as described in the approached of the present subject matter may correspond with the calibrated values of colours and contrasts of the anaglyph glasses. However, other dissociative glasses and/or techniques like polaroid glasses, virtual reality model for providing two different inputs to both the eyes may also be used, without deviating from the scope of the present subject matter.

Returning to the present example, prior to performing the activity, the eye care practitioner may monitor clinical parameters of the user's eyes. The eye care practitioner may monitor the clinical parameters and may provide a set of initial values of the element attributes 222 of the two sets of visual elements. For example, based on the severity of amblyopia in either of the eyes, the values of the element attributes may be determined. In cases where the user's eye is suffering from severe visual disorder, the size of the visual elements may be larger. Further, the spatial frequency, i.e., the distribution of the elements on the screen may also be less. In cases where the user's eye may have less visual disorder, the value of element attributes may be determined in such a manner so as to force the user's eye to focus on the visual elements in a strict manner. In one example, the amblyopic eye may be subjected to high contrast visual elements, whereas the non-amblyopic eye may be subjected to low contrast visual elements.

In one example, the eye care practitioner may monitor the clinical parameters of the user using a log MAR chart. The visual acuity of the user may be assessed using conventional approaches with a log MAR chart, and the element attributes 222 may correlate the viewing distance of the user with the size of the displayed visual elements.

Returning to the present example, the visual task module 214, based on the determined set of element attributes 222, may generate display signals. The display signals may then display the two sets of visual elements 218 and 220 on the display device 202 in the determined manner. As mentioned previously, the two sets of visual elements may be a part of the series of dynamically changing visual challenges and tasks intended for the user.

The computing device 200 may then prompt the user to provide a response. The user may provide the response to the computing device 200 through a peripheral device (not shown in FIG. 2). Examples of such responses from the peripheral devices may include, but are not limited to, pressing a key from the keyboard, clicking the mouse, and touching the screen.

As would be understood, the two sets of visual elements displayed on the display device 202 comprising the visual challenges and tasks in the activity may prompt the user to provide a response at every stage of the activity. The visual task module 214 may then compare and assess the user's responses using a pre-defined assessment criteria 228, to ascertain whether the user's response is correct or not, and also determine how quickly the response was provided by the user. The visual task module 214 may determine to ascertain the accuracy of user's responses for a pre-defined number of times.

It should be noted that the pre-defined assessment criteria 228 for assessing the user's responses may be specific to each therapeutic activity. The pre-defined assessment criteria may contain a set of pre-defined rules and range of values, based on which the visual task module 214 may determine a new set of values of element attributes 222, upon receiving a series of correct responses by the user. The visual task module 214, based on the modified set of element attributes 222, may generate corresponding display signals to display the modified set of visual elements.

In one example, when the user provides a series of correct responses, the visual task module 214 modifies the element attributes 222, i.e., size, spatial frequency, contrast and speed of the two sets of visual elements in such a manner, so as to increase the difficulty of the visual challenges of the therapeutic activity. In another example, the visual task module 214 may provide the user with a progress report, before displaying the new set of visual elements. In yet another example, the visual task module 214 may send the user's progress report over the network to the eye care practitioner, and the user may need to consult the eye care practitioner.

In this manner, every time the user provides a series of correct responses, the visual task module 214 modifies the element attributes 222 of the two sets of visual elements, and thereafter cause the modified set of visual elements to be displayed. As a result, as the activity progresses, and the correct responses increase, the successive sets of modifying visual elements cause the amblyopic eye, i.e., the weak eye to focus on the visual elements, thereby improving the visual acuity of the user.

In another example, for improving the fusional capability and stereoscopic acuity of the user, the visual task module 214, in response to the initiation by the user, may generate visual elements comprising a pair of images 224 separated with each other by an offset. The visual elements may be a part of series of dynamically changing visual challenges and tasks intended for the user. The two images of each of the visual elements may be defined based on a certain offset value 226. The offset is such that it, along with a notional line passing through the two eyes of the user, lies in the same horizontal plane.

The user may be provided with a dissociative glasses to interact and engage with the visual elements displayed on the display device 202. The pair of images 224 of a visual element may be provided in such a manner, that the visual element when viewed through the pair of dissociative glasses, may appear at a certain depth to the user. The user may be required to view the visual elements at a viewing direction which is perpendicular to that of the display screen 202. The offset value 226 of the pair of images of a visual element may control the depth at which the visual element may be displayed to the user.

However, any techniques other than dissociative glasses may also be used for displaying the visual elements to the user at certain depth without deviating from the scope of the present subject matter.

Returning to the present example, prior to performing the activity, the eye care practitioner may monitor clinical parameters of the user's eyes and may provide the initial offset value 226 for the pair of images 224 of a visual element. In one example, the eye care practitioner may monitor the viewing distance and interpupillary distance of the user's eyes for determining the initial offset value 226.

The visual task module 214, based on the determined offset value 226 may generate display signals for displaying the visual element comprising the two images 224 on the display device 202. As mentioned previously, the two sets of visual elements may be a part of the series of dynamically changing visual challenges and tasks intended for the user.

The computing device 200 may then prompt the user to provide a response. The user may provide the response to the computing device 200 through a peripheral device (not shown in FIG. 2). Examples of such responses from the peripheral devices may include, but are not limited to, pressing a key from the keyboard, clicking the mouse, and touching the screen.

As would be understood, the visual elements at certain different depths comprising the visual challenges and tasks may be designed in such a manner that it may provide the user to provide a response at every successive stage of the activity. On receiving the user's response, the visual task module 214 may then compare and assess the user's responses using a pre-defined assessment criteria 228, to ascertain whether the user's response is correct or not.

The pre-defined assessment criteria 228 may contain a set of pre-defined rules and range of values, based on which the visual task module 214 may determine a new offset value of at least one of the visual elements, upon receiving a correct response by the user. The visual task module 214, based on the modified offset value 226, may generate corresponding display signals to display the modified pair of images of the visual elements.

In one example, when the user provides a correct response, the visual task module 214 modifies the offset value 226 in such a manner, so as to increase the depth between the visual elements displayed on the screen. In another example, the visual task module 214 may provide the user with a progress report, before displaying the new set of visual elements. In yet another example, the visual task module 214 may send the user's progress report over the network to the eye care practitioner, and the user may need to consult the eye care practitioner.

In this manner, every time the user provides a correct response, the visual task module 214 modifies the offset value 226 of the two images 224 of visual elements, and thereafter cause the modified set of visual elements to be displayed at different depths. As a result, as the activity progresses, and the correct responses increase, the successive sets of modifying visual elements cause the user's eyes to improve its fusional capability and stereoscopic acuity, thereby developing and improving the binocular vision.

Figure 3:
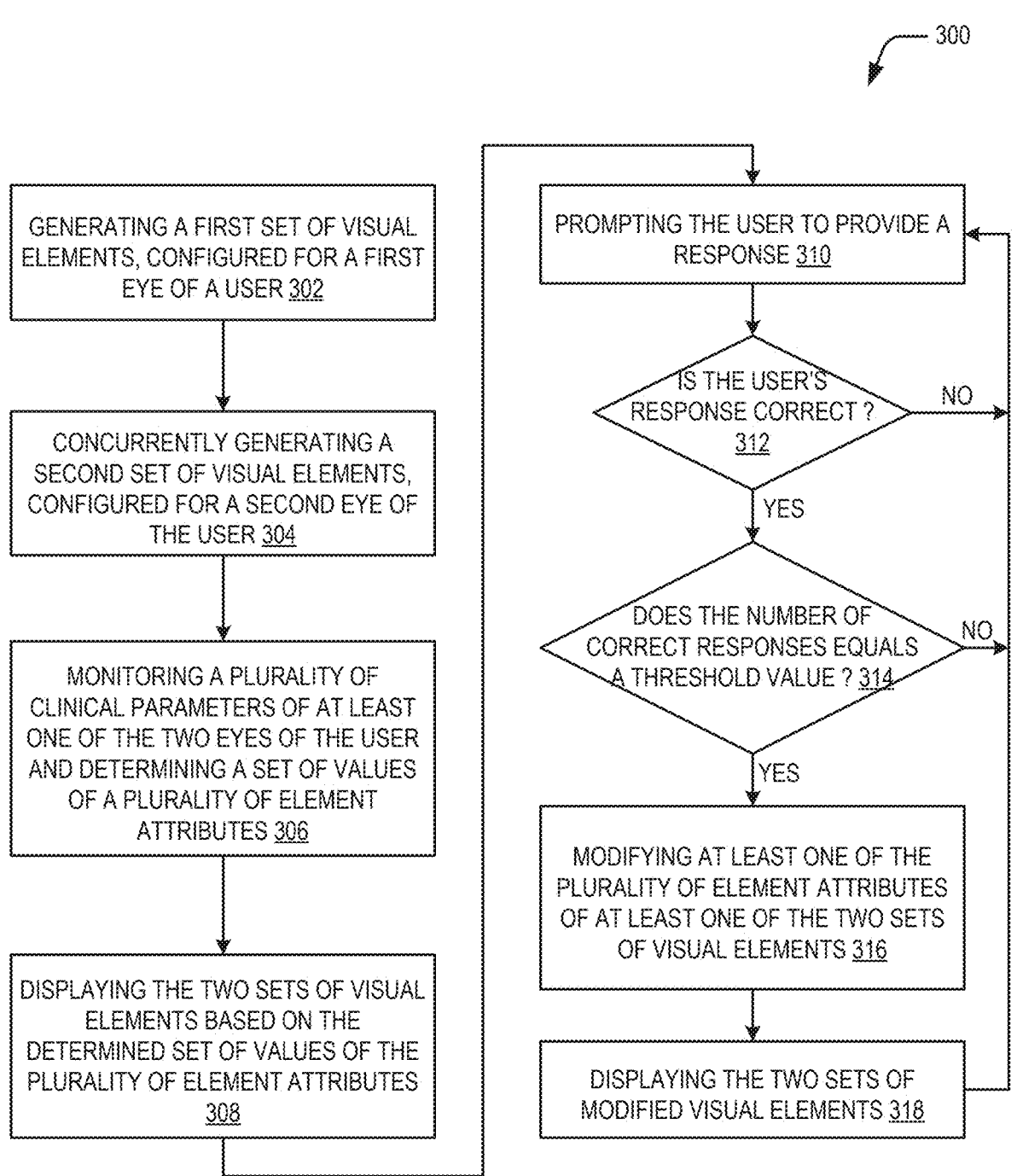
FIG. 3 is a flowchart depicting an example method for implementing therapeutic activities for management of binocular vision disorders in an example computing device, in accordance with an example of the present subject matter.

FIG. 3 is a flowchart depicting an example method for implementing therapeutic activities for improving the visual acuity of the user for management of binocular vision disorders, to be implemented in an exemplary computing device, in accordance with an example of the present subject matter. The order in which the method 300 is described is not intended to be construed as a limitation, and any number of the described method blocks may be combined in any order to implement the aforementioned method, or an alternative method. Furthermore, method 300 may be implemented by processing resource or computing device(s) through any suitable hardware, non-transitory machine-readable instructions, or combination thereof.

It may also be understood that method 300 may be performed by programmed computing devices as depicted in FIG. 1 or 2. Furthermore, the method 300 may be executed based on instructions stored in non-transitory computer readable medium, as will be readily understood. The non-transitory computer readable medium may include, for example digital memories, magnetic storage media, such as one or more magnetic disks and magnetic tapes, hard drives, or optically readable digital data storage media. Although, the method 300 is described below with reference to the computing device 200 as described above, other suitable systems for the execution of these methods can also be utilized. Additionally, implementation of this method is not limited to such examples.

At block 302, a first set of visual elements, configured for a first eye of a user may be generated. For example, the user or any other authorized individual may initiate one of the plurality of therapeutic activities for management of binocular vision disorders. As would be understood, the activity may include a series of visual challenges and tasks to be performed by the user for improving the visual acuity. The therapeutic activity may be designed in such a way, that the visual task module (as described in FIG. 2) may generate two different sets of visual elements 218 and 220 to be displayed on the display device 202, in such a manner that the user when perform the activity with a pair of dissociative glasses, may tend to receive different visual inputs to both the eyes. Examples of such dissociative glasses may include, but are not limited to, a pair of anaglyph glasses and polaroid glasses At block 304, a second set of visual elements, configured for a second eye of the user may be generated concurrently. For example, the visual task module 214 may also generate a second set of visual elements 220. Further, both the sets of visual elements may include different visual characteristics. Examples of such visual characteristics include chromaticity and polarity. In one example, the user may perform the therapeutic activity with a pair of chromatically different coloured anaglyph glasses. In such cases, the different visual characteristics of both the sets of visual elements may correspond to the two sets of visual elements of the same colour as that of anaglyph glasses.

At block 306, clinical parameters of at least one of the two eyes of the user may be monitored, and a set of values of element attributes may be determined. For example, prior to performing the activity, the eye care practitioner may monitor clinical parameters of the eyes of the user. The two sets of visual elements may comprise element attributes 222. The element attributes 222 may include size, contrast, spatial frequency and size of the two sets of visual elements. The visual task module 214 may allow the user to determine a set of values of the element attributes 222 corresponding to the clinical parameters of the user, i.e., the visual task module 214 may allow the user to initiate the activity in a convenient manner corresponding to the clinical conditions of the user.

At block 308, the two sets of visual elements may be displayed based on the determined set of values of the element attributes. The element attributes 222 may control the manner in which the two sets of visual elements may be displayed on the display device 202. For example, the user may be subjected to visual elements of high contrast to the weak eye, and comparatively low contrast to the normal eye. The visual task module 214 may generate display signals corresponding to the values of element attributes 222 of the two sets of visual elements. The display signals may then cause to display the two sets of visual elements 218 and 220 on the display device 202. In one example, the eye care practitioner may assess the visual acuity of the user using log MAR chart, and thereafter the values of element attributes 222 may correlate to the assessed values of user's visual acuity.

At block 310, the user may be prompted to provide a response. As mentioned previously, the therapeutic activity may include a series of visual challenges and tasks for the interaction of user. The user may be required to provide a response to the computing device 200 at every stage of the therapeutic activity. For example, based on the displayed set of visual elements, the user may provide a response through a peripheral device. Examples of such responses from the peripheral devices may include, but are not limited to, pressing a key from the keyboard, clicking the mouse, and touching the screen.

At block 312, a determination may be made to ascertain whether the user's response is correct or not. For example, the visual task module 214, on receiving the response from the user may compare the user' response using a pre-defined assessment criteria to ascertain whether the user's response is correct or not, and also determine how quickly the response was provided by the user. As mentioned previously, the pre-defined assessment criteria 228 may contain a set of pre-defined rules and range of values, based on which the visual task module 214 may determine a new set of values of element attributes 222, upon receiving a series of correct responses by the user. If the user's response is incorrect ('No' path from block 312), the visual task module 214 may again prompt the user to provide a response (block 310). However, if the user's response is correct ('Yes' path from block 312), the method may proceed to block 314.

At block 314, a further determination may be made to ascertain whether the number of correct responses equals a threshold value. For example, the visual task module 214, before proceeding further in the method 300, may require the user to provide a series of correct responses corresponding to a pre-defined threshold value. If the number of correct responses from the user does not match a pre-defined threshold value ('No' path from block 314), the visual task module 214 may again prompt the user to provide a response (block 310). The visual task module 214 may recursively prompt the user to provide responses, till the time the user provides a series of correct responses corresponding to the threshold value. If the number of correct responses equals a threshold value ('Yes' path from block 314), the method proceeds to block 316.

At block 316, at least one of the plurality of element attributes of at least one of the two sets of visual elements may be modified. For example, in the cases where the number of correct responses by the user equals a threshold value, the visual task module 214, according to a set of pre-defined rules, may modify the element attributes 222 of at least one of the two sets of visual elements 218 and 220. In one example, the visual task module 214, on determining a series of correct responses by the user, may modify one of the element attributes 222 of at least one of the two sets of visual elements. In another example, the visual task module 214, on receiving a series of correct responses by the user, may modify the element attributes 222 in such a manner, that it may increase the difficulty level of the visual challenges and tasks in the therapeutic activities.

At block 318, the two sets of modified visual elements may be displayed. For example, the visual task module 214, based on the modified set of values of element attributes 222, may generate display signals. The display signals may then cause to display the two sets of visual elements on the display device 202. The visual task module 214 may then again prompt the user to provide a response (block 310). In this manner, the therapeutic activities may continue to provide the user with a series of visual challenges and tasks to perform with a set of visual elements. The user may keep providing a series of correct responses and the visual task module 214 may continue to modify the element attributes 222 of the two sets of visual elements, and thereafter display the modified sets.

Figure 4:
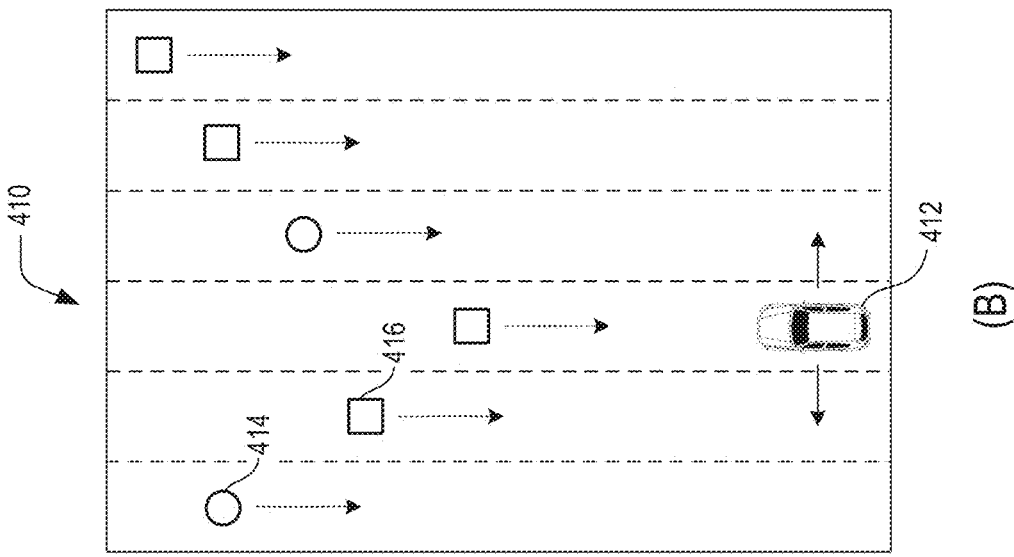
FIG. 4 depicts a diagram of an exemplary therapeutic activity for management of binocular vision disorders, as per an example of the present subject matter.
Figure 4:
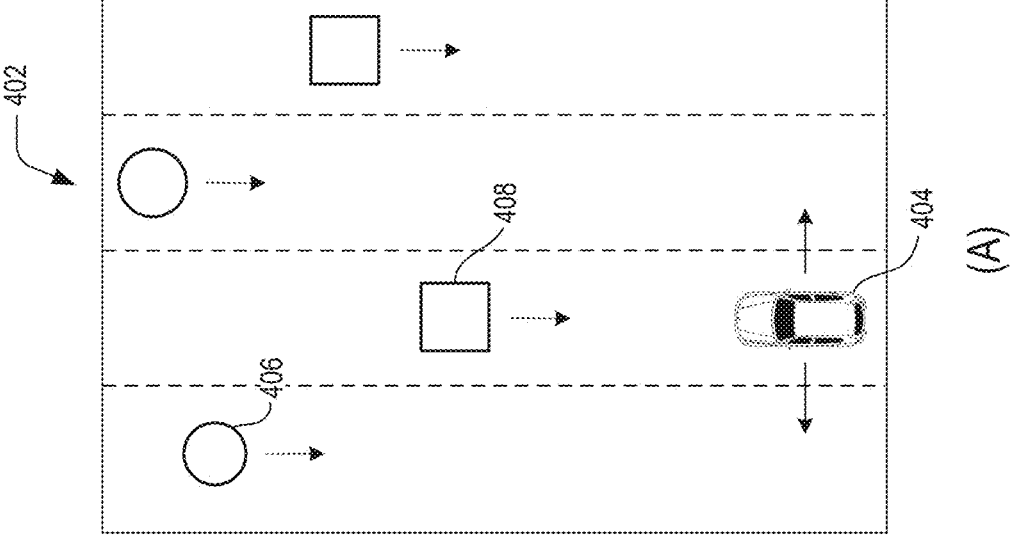

FIG. 4 depicts a diagram of an exemplary therapeutic activity for management of binocular vision disorders, to be implemented on a computing device 200 as described in FIG. 2, as per an example of the present subject matter. The aforementioned activity is performed in cases, where the user may be suffering from amblyopia and suppression, and binocular vision of the user's eyes is improper. Specifically, the approaches provided in the present exemplary therapeutic activity may be used by an eye care practitioner for improving the visual acuity of the user. It may be noted that, the exemplary activity, as described below in further details is only one of the plurality of therapeutic activities provided by the visual task module 214.

Upon initiation by the user, the visual task module 214 may display a set of visual challenges and tasks on the display device 202 in an initial manner 402. As described previously, the eye care practitioner may monitor clinical parameters of the user and cause the visual challenges and tasks to be displayed on the display device 202 based on a set of values of element attributes. In one example, the eye care practitioner may assess the visual acuity of the user with a log MAR chart. In such cases, the result of the log MAR chart may determine the values of the element attributes 222.

As shown in illustration 402, the visual task module 214 may cause a plurality of objects 406 and 408 to be displayed on the display device 202. The element attributes 222, as described previously, may include size and contrast of the visual objects 406 and 408. The element attributes 222 may further include the spatial frequency of the objects 406 and 408 on the display device 202, i.e., the number of objects displayed on the display device 202. In one example, the size of the objects 406 and 408, measures in pixels, may be based on the value of visual acuity as measured by the log MAR chart.

Although the present example is depicted using a plurality of circles 406 and squares 408, the same should not be considered as a limitation and any other shapes like triangle, square, rectangle or any other geometrical shape may be used to perform the activity. Further, the aforementioned therapeutic activity may be performed using a pair of dissociative glasses such that both eyes receive different visual inputs. However, any other techniques like polaroid glasses or a virtual reality model for providing different inputs to both the eyes may also be used without deviating from the scope of the present subject matter.

Returning to the present example, the objects 406 and 408 may be made to move from the top of the screen to towards the bottom, in a vertical manner. To such an extent, the element attributes 222 may further include the value of speed at which the objects 406 and 408 may move from top to bottom of the screen. The visual task module 214 may further cause a vehicle shaped object 404 to be displayed along the bottom of the screen. The vehicle 404 may be movable along the horizontal direction in the bottom of the screen.

As mentioned previously, the displayed set of visual elements, i.e., 404, 406 and 408 on the display device may comprise different visual characteristics. In the cases where the user is performing the activity with a pair of anaglyph glasses, the two sets of visual elements may correspond to chromatically different coloured elements. In one example, the vehicle 404 may comprise first visual characteristic, i.e., may be of first colour, and the objects 406 and 408 may be of second colour. However, any other combinations of different visual characteristics of the set of visual elements may be possible, without deviating from the scope of the present subject matter.

In operation, upon initiation by the user, the visual task module 214 may display the set of visual elements, i.e., the objects 406 and 408 on the display device 202 based on a set of values of element attributes. Thereafter, the visual task module 214 may prompt the user to provide a response. As described in FIG. 4, the objects 406 and 408 may move from the top of the screen to the bottom in a vertical manner. The vehicle 404 may be movable across the bottom of the screen in a horizontal manner.

The visual challenges, as described in FIG. 4, may be designed in such a manner, may require the user to use a user-controlled visual element to catch one of the plurality of objects, say 406 and avoid the second plurality of objects, i.e. 408 with the vehicle 404. The user may provide the inputs through the peripheral device. As the activity progresses, the visual task module 214 may consider the user's response to be correct, in cases where the user catches the desired set of objects and avoids the other set of movable objects using the vehicle 404. Upon receiving a series of correct responses by the user, the visual task module 214 may modify the element attributes 222 of the objects 406 and 408.

As shown in illustration 410, the visual task module may modify the element attributes 222 of at least one of the two sets of visual elements. In the foregoing example, the visual task module 214 may decrease the size of the objects 406 and 408, based on log MAR values and display them as objects 414 and 416 respectively. Further, the visual task module may increase the number of objects 414 and 416 on the screen, Furthermore, the visual task module 214 may also increase the speed at which the objects 414 and 416 fall from the top of the screen towards the vehicle 412, as well as may modify the contrast variation between the objects 414 and 416.

The visual task module 214 may then again prompt the user to provide a response. The user may again provide a series of correct responses, and the visual task module 214 may again modify at least one of the element attributes 222 of the two sets of visual elements, i.e., 414 and 416.

In one example, the visual task module 214 may provide the user with a progress report before displaying the modified set of visual elements. In another example, the visual task module 214 may send the user's progress report over the network to an eye care practitioner and the user may then need to consult the eye care practitioner for the prescribed treatment.

The approaches described in the aforementioned therapeutic activity for management of binocular vision disorders may provide the user with an enhanced approach over conventional occlusion therapy. The visual task module 214 may simultaneously provide two sets of visual elements in such a manner, that only one of the visual elements may be displayed to each of the two eyes. As a result, the aforementioned activity not only treats the visual disorder of the amblyopic eye, but also develop and improves the fusional capability and depth perception ability of the user.

It may also be noted that modifying the element attributes such as size, contrast, spatial frequency and size of the two sets of visual elements as the activity progresses, enables the user for a neuro-vision development in a better manner.

Figure 5:
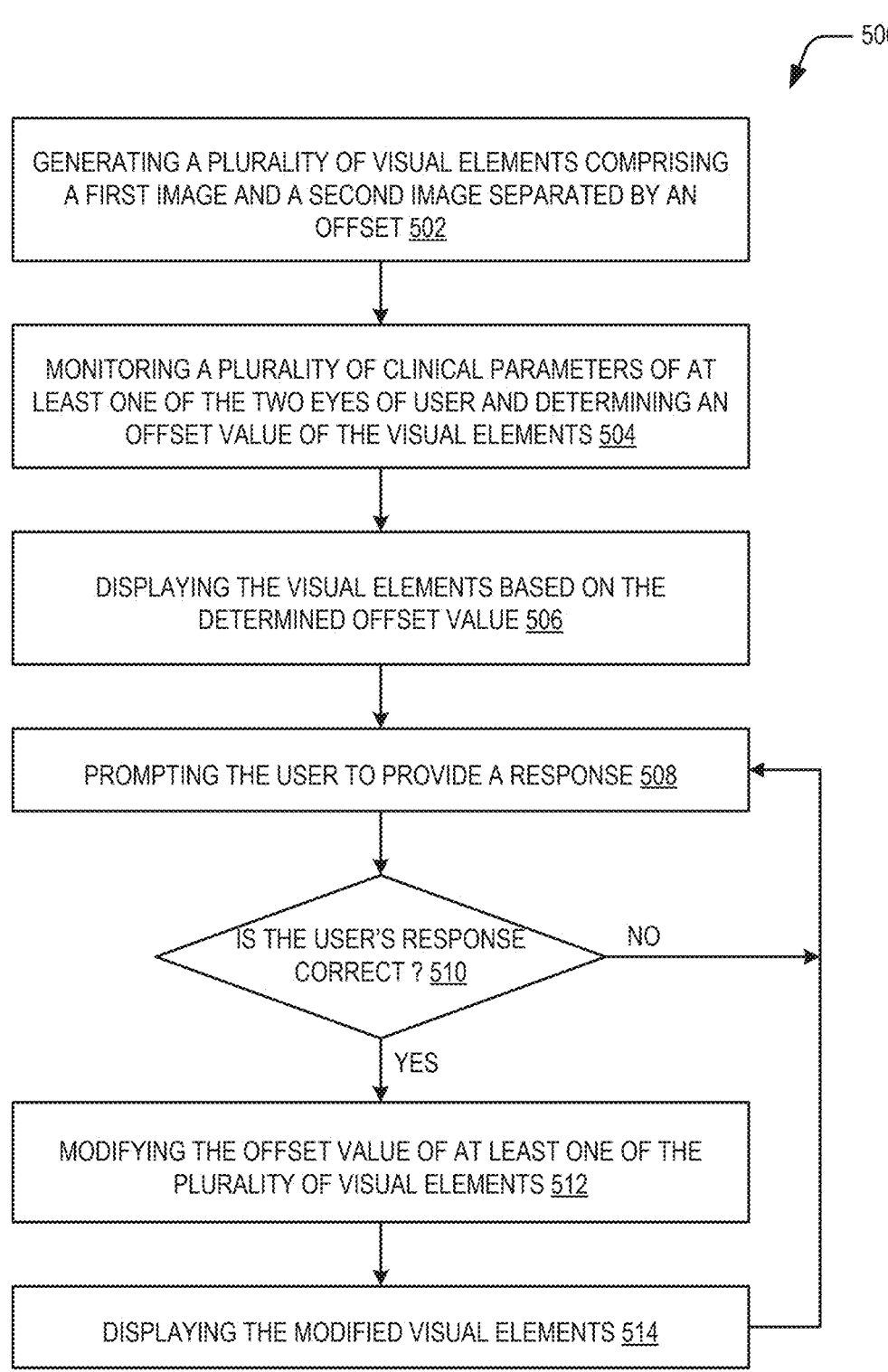
FIG. 5 is a flowchart depicting an example method for implementing therapeutic activities for management of binocular vision disorders in an example computing device, in accordance with another example of the present subject matter.

FIG. 5 is a flowchart depicting an example method for implementing therapeutic activities for improving the stereoscopic acuity of the user for management of binocular vision disorders, to be implemented in an exemplary computing device, in accordance with another example of the present subject matter. The order in which the method 500 is described is not intended to be construed as a limitation, and any number of the described method blocks may be combined in any order to implement the aforementioned method, or an alternative method. Furthermore, method 500 may be implemented by processing resource or computing device(s) through any suitable hardware, non-transitory machine-readable instructions, or combination thereof.

It may also be understood that method 500 may be performed by programmed computing devices as depicted in FIG. 1 or 2. Furthermore, the method 500 may be executed based on instructions stored in non-transitory computer readable medium, as will be readily understood. The non-transitory computer readable medium may include, for example digital memories, magnetic storage media, such as one or more magnetic disks and magnetic tapes, hard drives, or optically readable digital data storage media. Although, the method 500 is described below with reference to the computing device 200 as described above, other suitable systems for the execution of these methods can also be utilized. Additionally, implementation of this method is not limited to such examples.

At block 502, a plurality of visual elements comprising a first image and a second image separated by an offset may be generated. For example, the user or any other authorized individual, after performing the activity as described in FIG. 4, may initiate one of the plurality of subsequent therapeutic activities. As would be understood, the activity may include a series of visual challenges and tasks to be performed by the user for improving the fusional capability and stereoscopic acuity. The visual task module 214 may generate visual elements comprising a pair of images 224 separated with each other at an offset.

At block 504, clinical parameters of at least one of the two eyes of the user may be monitored, and an offset value of the two images of the visual elements may be determined. For example, prior to performing the activity, the eye care practitioner may monitor clinical parameters of the eyes of the user. In one example, the eye care practitioner may monitor the viewing distance and interpupillary distance of the eyes of the user, and a corresponding offset value may be determined. The offset is such that it, along with a notional line passing through the two eyes of the user, lies in the same horizontal plane. Further, the determined offset value 226 of the two images of a visual element may control the depth at which the corresponding visual element may appear to the user.

At block 506, the visual elements may be displayed based on the determined offset value of the pair of images. For example, the user may be provided with dissociative glasses to interact and engage with the visual elements being displayed on the screen. The visual task module 214 may generate display signals corresponding to the offset value 226 of the pair of images 224 of the sets of visual elements. The two images 224 of the visual elements may be displayed on the display device in such a manner, that when viewed through a pair of dissociative glasses may appear at a certain depth to the user. The user may be required to view the visual elements at a viewing direction perpendicular to that of the display device 202.

At block 508, the user may be prompted to provide a response. As mentioned previously, the therapeutic activity may include a series of visual challenges and tasks for the interaction of user. The user may be required to provide a response to the computing device 200 at every stage of the therapeutic activity. For example, based on the displayed visual elements, the user may provide a response through a peripheral device. Examples of such responses from the peripheral devices may include, but are not limited to, pressing a key from the keyboard, clicking the mouse, and touching the screen.

At block 510, a determination may be made to ascertain whether the user's response is correct or not. For example, the visual task module 214, on receiving the response from the user may compare the user' response using a pre-defined assessment criterion to ascertain whether the user's response is correct or not. As mentioned previously, the pre-defined assessment criteria 228 may contain a set of pre-defined rules and range of values, based on which the visual task module 214 may determine a new offset value 226, upon receiving a correct response by the user. If the user's response is incorrect ('No' path from block 510), the visual task module 214 may again prompt the user to provide a response (block 508). However, if the user's response is correct ('Yes' path from block 510), the method may proceed to block 512.

At block 512, the offset value of at least one of the visual elements may be modified. For example, in the case where the user's response is correct, the visual task module 214, according to a set of pre-defined rules, may modify the offset value 226 of the pair of images 224 of at least one of the visual elements. The offset value may be modified in such a manner, that the visual elements may now appear to the user at a different depth.

At block 514, the modified visual elements may be displayed. For example, the visual task module 214, based on the modified offset value, may generate display signals. The display signals may then cause to display the modified visual elements on the display device 202. The visual task module 214 may then again prompt the user to provide a response (block 508). In this manner, the therapeutic activities may continue to provide the user with a series of visual challenges and tasks to perform with visual elements comprising a pair of images, at a certain stereoscopic depth. The user may keep providing correct response and the visual task module 214 may continue to modify the offset value of the visual elements, and thereafter display the modified visual elements.

Figure 6:
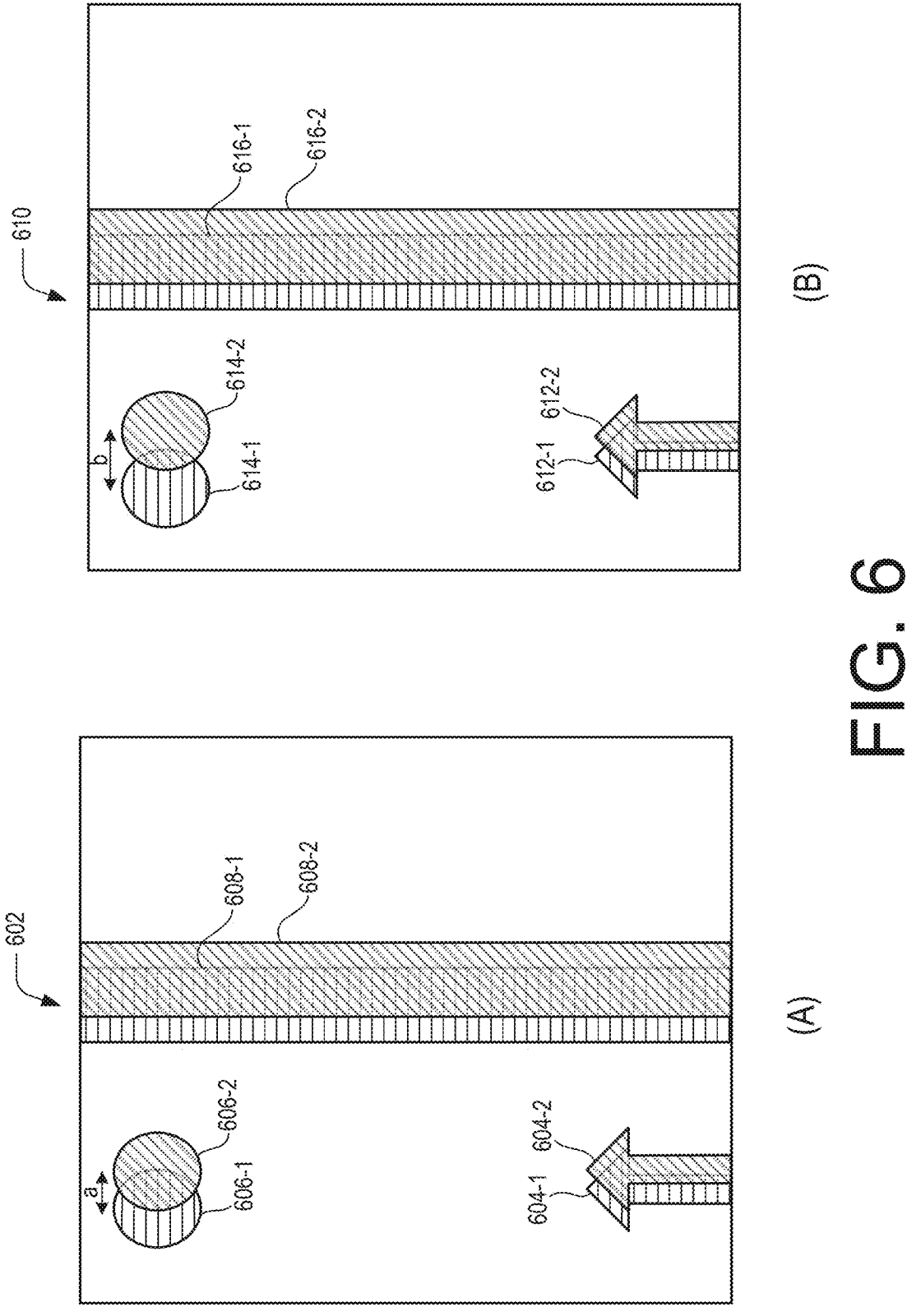
FIG. 6 depicts a diagram of an exemplary therapeutic activity for management of binocular vision disorders, as per another example of the present subject matter.

FIG. 6 depicts a diagram of an exemplary therapeutic activity for management of binocular vision disorders, to be implemented on a computing device 200 as described in FIG. 2, as per another example of the present subject matter. The aforementioned activity is performed in cases, where the user may be suffering from amblyopia and suppression, and binocular vision of the user's eyes is improper. Specifically, the approaches provided in the present exemplary therapeutic activity may be used by an eye care practitioner for improving the fusional capability and stereoscopic acuity of the user. It may be noted that, the exemplary activity, as described below in further details is only one of the plurality of therapeutic activities provided by the visual task module 214.

Upon initiation by the user, the visual task module 214 may display a set of visual challenges and tasks on the display device 202 in an initial manner 602. As described previously, the eye care practitioner may monitor clinical parameters of the user and cause the visual challenges and tasks to be displayed on the display device 202 based on an offset value. In one example, the eye care practitioner may assess the viewing distance and interpupillary distance of the user's eyes. In such cases, such measures parameters may determine the initial offset value of the visual elements.

As shown in illustration 602, the visual task module 214 may cause a plurality of visual elements 604, 606 and 608 to be displayed on the display device 202. The visual challenges and tasks may be designed in such a way, that each of the visual element may comprise a pair of images separated by a certain offset. For example, the visual element 606 comprises a pair of images 606-1 and 606-2. In a similar manner, the visual elements 604 may comprise a pair of images 604-1 and 604-2, and the visual element 608 may comprise images 608-1 and 608-2 separated by a certain offset.

The user may be provided with a pair of dissociative glasses for engaging and interacting with the visual elements displayed on the screen. The pair of images of each of the visual elements may cause the corresponding visual element to appear at a certain depth, when viewed through a pair of dissociative glasses to the user. In one example, the size of the visual elements may be determined by the eye care practitioner based on the viewing distance of the user.

In one example, the user may view the visual elements with a pair of anaglyph glasses. In such cases, the visual elements may comprise chromatically different coloured images based on the colour filters of anaglyph glasses.

The visual challenge may be designed in such a manner, that the pair of images of the visual elements 606 and 608 may be separated by different values of offset, such that the visual elements 606 and 608 may appear at different depths, when viewed through the dissociative glasses, to the user.

The visual element 606 may comprise a pair of images 606-1 and 606-2 separated by an offset value 'a', i.e., the visual element 606 may appear at a certain stereoscopic depth to the user corresponding to the offset value 'a'. Further, the visual challenge may comprise a visual element 604, at another offset value, i.e., at another stereoscopic depth. Furthermore, the visual challenge may comprise yet another visual element 608 positioned along the center of the display device 202.

In operation, upon initiation by the user, the visual task module 214 may display the pair of images of respective visual elements 604 and 606 on the display device 202 at different offsets. Therefore, the visual elements 604 and 606 may appear to the user at different depths. Thereafter, the visual task module 214 may prompt the user to provide a response. The user may provide the inputs through the peripheral device.

The visual challenges, as described in FIG. 6, may be designed in such a manner, may require the user to match the depth of the visual element 604, with the depth of the visual element 606. The visual element 606 may appear to the user at a pre-defined depth, corresponding to the offset value 'a'. The user may be required to adjust the offset value of the visual element 604, in such a manner, to match the stereoscopic depth of the visual element 604 with that of the visual element 606. Once the user has aligned the depth of both of the visual elements 604 and 606, the visual challenge may allow the user to shoot an arrow, i.e., the visual element 604 to strike the sphere, i.e., the visual element 606.

As the activity progresses, the visual task module 214 may consider the user's response to be correct, in cases where the user matches the perceived depth of the visual element 604, to the depth of the visual element 606. Upon receiving a correct response by the user, the visual task module 214 may modify the offset value of the pair of images of visual element 606, so as to modify its depth.

As shown in illustration 610, the visual task module may modify the offset value of at least one of the visual elements. In the foregoing example, the visual task module 214 may modify the offset value of the two images of visual element 606 and display them as images 614-1 and 614-2 with an offset value 'b'. The visual element 606 may then appear to the user at a different depth. The visual task module 214 may modify the offset value of one of the visual elements in such a manner, so as to increase the difficulty of the visual challenge.

The visual task module 214 may then again prompt the user to provide a response. The user may again provide a correct response, and the visual task module 214 may again modify the offset value of at least one of the visual elements.

Further, a visual element 608, positioned along the center of the screen, may enable the user's eyes to fuse on the stereoscopic visual elements in a better manner. As would be understood, human brain tends to focus on the biggest visual element along the center of the screen. The visual element 608 may be provided to the user for improving the fusional capability of the user's eyes.

In one example, as the activity progresses, the offset value, i.e., the perceived depth of the vertical bar 608 may modify in accordance with the offset value of the visual element 606. In such cases, the approaches provided in the present subject matter may allow the user to improve on its fusional capability, as well as stereoscopic depth in a better manner. In another example, in cases where the user's condition improves, the vertical visual element 608 may be subjected to the user at a fixed depth, and only the fusion of the visual element 606 changes.

Although the present example is depicted using an arrow 404, a sphere 406 and a centrally placed dominant vertical bar 408, the same should not be considered as a limitation and any other shapes like triangle, square, rectangle or any other geometrical shape may be used to perform the activity. The visual challenge may be designed in such a manner, that it may require a dominant object for helping the brain to fuse, a reference visual object at a pre-defined depth, and an object with varying offset for receiving the input from the user. The user may be required to match the perceived depth of the visual object, to the depth of the reference object.

Further, the aforementioned therapeutic activity may be performed using a pair of polaroid glasses, a virtual reality model, or any other technique such that the visual elements may appear to the user at certain depths, without deviating from the scope of the present subject matter.

In one example, the visual task module 214 may provide the user with a progress report before displaying the modified set of visual elements. In another example, the visual task module 214 may send the user's progress report over the network to an eye care practitioner and the user may then need to consult the eye care practitioner for the prescribed treatment.

The approaches described in the aforementioned therapeutic activity for management of binocular vision disorders may provide the user with an enhanced approach for developing and improving the fusional capability, as well as stereoscopic acuity of the user. The visual task module 214 may provide the visual elements in such a manner, that when viewed through a pair of dissociative glasses, may appear at a certain depth to the user. As a result, the approaches provided in the present subject matter assess the stereoscopic acuity of the user, i.e., depth perception ability, and improves the same.

It may also be noted that providing the user with a dominant visual element positioned along the center of the screen allows the user's brain to fuse the incoming images, and thereby improves the fusional capability of the user's brain.

It may be further noted that, the exemplary therapeutic activities for management of binocular vision disorders as described in conjunction with FIGS. 4 and 6 are only for the purpose of illustrations of one of the plurality of activities provided by the visual task module 214. As described above, the activity provided in conjunction with FIG. 4 improves the visual acuity of the user, and the activity provided in conjunction with FIG. 6 improves the fusional capability and stereoscopic acuity of the user. An amblyopic patient may be subjected to a series of visual challenges for improving the visual acuity, and then improving the fusional capability and stereoscopic acuity.

Furthermore, any combination of any type of visual elements with a set of values of element attributes may be used to implement the aforementioned therapeutic activities for the management of binocular vision disorders, without deviating from the scope of the present subject matter.

An example setup is now described depicting the results of the therapeutic activities conducted on a set of amblyopic patients in accordance with the present subject matter. As mentioned previously, the patient may be suffering from binocular vision disorder, i.e., amblyopia and suppression. A set of amblyopic patients were subjected to a series of visual challenges and tasks comprising the therapeutic activities as described above. The patients were chosen in such a manner, that none of the patients had eccentric fixation in their eyes. As would be understood, in eccentric fixation, the patient may utilize a portion of retina other than fovea for fixation. In such cases, the patient on being subjected to the therapeutic activities as described above in the present subject matter may not yield any results.

The set of patients were subjected to the dichoptic sessions comprising the visual challenges and tasks of 1 hour per day for 5 days a week. The therapeutic activities were conducted by the eye care practitioner for 6 weeks, for improving the visual acuity, fusional capability and stereoscopic acuity of the patient.

In one example, 119 patients suffering from anisometropic amblyopia with a median age of 9 years were subjected to 30 dichoptic sessions of the therapeutic activities for improving the visual acuity. As would be understood, anisometropic amblyopia may develop in the patient when the refractive errors in the two eyes of the patient may not be equal. After a series of such activities, the median Best Corrected Visual Acuity (BCVA) was improved from 0.60 Log MAR to 0.24 Log Mar.

In another example, 31 patients suffering from isometropic amblyopia with a median age of 7 years were subjected to 30 dichoptic sessions of the therapeutic activities for improving the visual acuity. As would be understood, isometropic amblyopia may develop in the patient when the refractive errors in the two eyes of the patient may equal. In the case of patient's right eye, after a series of such activities, the median Best Corrected Visual Acuity (BCVA) was improved from 0.48 Log MAR to 0.14 Log Mar. In the case of patient's left eye, after a series of such activities, the median Best Corrected Visual Acuity (BCVA) was improved from 0.50 Log MAR to 0.16 Log Mar.

In yet another example, 103 patients suffering from anisometropic amblyopia and absence of stereoscopic acuity were subjected to 30 dichoptic sessions of the therapeutic activities for improving the stereoscopic acuity. 87 out of 103 patients were able to develop a median stereoscopic acuity of 300 seconds of arc. In yet another example, 7 patients suffering from isometropic amblyopia and absence of stereoscopic acuity were subjected to 30 dichoptic sessions of the therapeutic activities for improving the stereoscopic acuity. 7 out of 7 patients were able to develop a median stereoscopic acuity of 400 seconds of arc.

Although examples for the present disclosure have been described in language specific to structural features and/or methods, it should be understood that the appended claims are not necessarily limited to the specific features or methods described. Rather, the specific features and methods are disclosed and explained as examples of the present disclosure.

What is claimed:

1. A computing device for managing amblyopia and suppression, the computing device comprising:
  a processor;
  a visual task module coupled to the processor, wherein the visual task module is to:
  generate, on a display device, a first visual element and a second visual element during a computer implemented therapeutic activity, wherein the computer implemented therapeutic activity for improving stereoscopic acuity comprises a plurality of stages, and wherein each of the first visual element and the second visual element comprises:
    a first image and a second image, separated by an offset, wherein the first and the second image have different visual characteristics, and wherein as a result of the offset between the first image and the second image of both the first visual element and the second visual element, the corresponding one of the first visual element and the second visual element are to appear at different stereoscopic depths, relative to each other, when viewed through a pair of dissociative glasses;
    prompt a user to provide a response at every stage of the computer implemented therapeutic activity;
    receive a series of responses during a respective stage of the computer implemented therapeutic activity from the user;
    based on the series of received user's response, modify the offset value between the first image and the second image of at least one of the first visual element and the second visual element during the computer implemented therapeutic activity,
    wherein modifying the offset value between the first image and the second image of at least one of the first visual element and the second visual element is to change the stereoscopic depth of the first visual element to match with the stereoscopic depth of the second visual element, when the two images are viewed by a user using the pair of dissociative glasses; and
    wherein modifying the offset value of the at least one of the first visual element and the second visual element during the computer implemented therapeutic activity to increase the level of difficulty of visual challenges comprises:
      comparing the series of user's responses, received during the said stage of the computer implemented therapeutic activity, using an assessment criteria for a pre-defined number of times;
      based on the comparison, determining a new offset value of the plurality of visual elements during the computer implemented therapeutic activity to correspond to an increased level of difficulty of the visual challenges; and
      based on the modified offset value, display the modified first visual element and the second visual element during a successive stage of the computer implemented therapeutic activity.

2. The computing device as claimed in claim 1, wherein the pair of dissociative glasses is a pair of anaglyph glasses or polaroid glasses.

3. The computing device as claimed in claim 1, wherein the two images of the visual elements comprise chromatically different coloured images during the computer implemented therapeutic activity.

4. The computing device as claimed in claim 1, wherein the offset is such that it, along with the notional line passing through the two eyes of the user, lies in the same horizontal plane and is based on viewing distance and interpupillary distance of the user during the computer implemented therapeutic activity.

5. The computing device as claimed in claim 1, wherein based on successive user's responses, the visual task module is to further render a progress report to the user during the computer implemented therapeutic activity.

6. A method for managing amblyopia and suppression, the method comprising:

generating, on a display device, a first visual element and a second visual element during a computer implemented therapeutic activity, wherein the computer implemented therapeutic activity for improving stereoscopic acuity comprises a plurality of stages, and wherein each of the first visual element and the second visual element comprises:

a first image and a second image, separated by an offset, wherein the first and the second image have different visual characteristics, and wherein as a result of the offset between the first image and the second image of both the first visual element and the second visual element, the corresponding one of the first visual element and the second visual element are to appear at different stereoscopic depths, relative to each other, when viewed through a pair of dissociative glasses;

prompting the user to provide a response at every stage of the computer implemented therapeutic activity;

receiving a series of responses during a respective stage of the computer implemented therapeutic activity from the user;

based on the series of received user's response, modifying the offset value between the first image and the second image of at least one of the first visual element and the second visual element during the computer implemented therapeutic activity, wherein modifying the offset value between the first image and the second image of at least one of the first visual element and the second visual element is to change the stereoscopic depth of the first visual element to match with the stereoscopic depth of the second visual element, when the two images are viewed by a user using the pair of dissociative glasses; and

wherein modifying the offset value of the at least one of the first visual element and the second visual element during the computer implemented therapeutic activity to increase the level of difficulty of visual challenges comprises:

comparing the series of user's responses, received during the said stage of the computer implemented therapeutic activity, using an assessment criteria for a pre-defined number of times;

based on the comparison, determining a new offset value of the plurality of visual elements during the computer implemented therapeutic activity to correspond to an increased level of difficulty of the visual challenges; and based on the modified offset value, displaying the modified first element and the second visual element during a successive stage of the computer implemented therapeutic activity.

7. The method as claimed in claim 6, wherein the user is to view the chromatically different two sets of visual elements through the corresponding pair of dissociative glasses during the computer implemented therapeutic activity.

8. The method as claimed in claim 6, wherein displaying the two sets of visual elements further comprises:

monitoring a plurality of clinical parameters of at least one of the two eyes of the user during the computer implemented therapeutic activity; and based on the monitored clinical parameters, determining a set of values of a plurality of element attributes.

9. The method as claimed in claim 6, wherein the first visual element and the second visual element comprise a contrast, size, spatial frequency and speed of the two sets of visual elements.

* * * * *